United States Patent [19]

Hassler et al.

[11] Patent Number: 4,478,083
[45] Date of Patent: Oct. 23, 1984

[54] PLANE RECONSTRUCTION ULTRASOUND TOMOGRAPHY DEVICE

[75] Inventors: Dieter Hassler, Uttenreuth; Elmar Trautenberg, Fuerth-Stakeln, both of Fed. Rep. of Germany

[73] Assignee: Siemens AG, Berlin and Munich, Fed. Rep. of Germany

[21] Appl. No.: 503,437

[22] Filed: Jun. 13, 1983

[30] Foreign Application Priority Data

Jun. 30, 1982 [DE] Fed. Rep. of Germany ....... 3224453

[51] Int. Cl.³ .......................................... G01N 29/00
[52] U.S. Cl. ...................................... 73/620; 73/612; 73/626; 128/660
[58] Field of Search ................ 73/597, 599, 607, 612, 73/614, 615, 618, 620, 621, 625, 626, 628, 641; 128/660

[56] References Cited

U.S. PATENT DOCUMENTS 4,105,018  8/1978  Greenleaf et al. .................... 73/597
4,272,991  6/1981  Cribbs ................................. 73/621

OTHER PUBLICATIONS

Fifth International Symposium on Ultrasonic Imaging and Tissue Characterization and Second International Symposium on Ultrasonic Materials Characterization, Jun. 1-6, 1980, p. 7.
Ultrasonic Imaging I, pp. 154-184 (1979), by Stephen J. Norton and Melvin Linzer.

*Primary Examiner*—Stephen A. Kreitman
*Attorney, Agent, or Firm*—Karl F. Milde, Jr.

[57] ABSTRACT

An ultrasound tomography device for scanning an object under examination from a plurality of directions. Coronal slice images of the plane areas near or at the female breast wall are obtained. Ultrasound lobes from ultrasound transducers are electronically directed or mechanically positioned to obliquely strike the coronal slice located at or near the breast wall. A full image of the coronal slice plane is reconstructed through section by section combination of the images obtained from the several ultrasound lobes.

13 Claims, 6 Drawing Figures

PLANE RECONSTRUCTION ULTRASOUND TOMOGRAPHY DEVICE

BACKGROUND OF THE INVENTION

The invention relates to an ultrasound tomography device for producing coronal slice views of female breast tissue.

Ultrasound tomography devices can be operated in accordance with the transmission as well as the reflection method. For example an ultrasound tomography device for transmission tomography (UCTT) is known through U.S. Pat. No. 4,105,018. Ultrasound tomography devices for reflection tomography (UCTR), on the other hand, are known through the essay "Resolution and Image Quality by Ultrasonic Echo Tomography: Experimental Approach" by E. Hundt, G. Maderlechner, E Kronmueller and E. Trautenberg from the "Fifth International Symposium on Ultrasonic Imaging and Tissue Characterization and Second International Symposium on Ultrasonic Materials Characterization", June 1-6, 1980, page 7 and through the essay "Ultrasonic Reflectivity Tomography: Reconstruction with Circular Transducer Arrays" by Stephen J. Norton and Melvin Linzer from "Ultrasonic Imaging 1", 1979, pages 154–184.

However, these known ultrasound tomography devices do not allow scanning close to the breast wall in the sense of generating a coronal slice image of tissue situated close to the breast wall during an examination of a female breast. The dimensions of the ultrasound transmitting/receiving system are such that they interfere with required positioning of the equipment close to the breast wall.

The breast wall is the area which lies generally parallel to and near the chest surface. Coronal slices are plane views of a female breast tissue where the planes are generally oriented parallel to the breast wall.

SUMMARY OF THE INVENTION

It is an objective of the present invention to disclose an ultrasound tomography device, which provides with a minimal of technical investment coronal slices close to the breast wall.

The present invention enables a section by section reconstruction of a coronal slice situated close to the breast wall, by combining several individual coronal slices which are slightly tilted toward each other. This is accomplished by adjusting the tilting angle of several transmitting/receiving ultrasound lobes and through a section by section acquisition of signal data related to each of the step adjustments. The combination and filtering of the composite data yields the final product representing a coronal slice image of tissue situated close to the breast wall.

The groups of ultrasound transducers may be of different designs. Ultrasound transducers can include converter elements, which are similar to linear arrays, arrays for electronically controlled sector scan, ring arrays or other comparable devices. The ultrasound transducer may also include a single ultrasound resonator (transducer), which may be part of a slowly rotating sector scanner. Preferred embodiments of this invention are described in the detailed description. In other preferred embodiments of this invention, the individual or groups of ultrasound transducers are provided with different apertures for focusing at different object depths.

Other features and advantages of the present invention will become apparent from the following description of the preferred embodiments, and from the claims.

For a full understanding of the present invention, reference should now be made to the following detailed description of the preferred embodiments of the invention and to the accompanying drawings.

DESCRIPTION OF THE PREFERRED EMBODIMENTS

Figure 1:
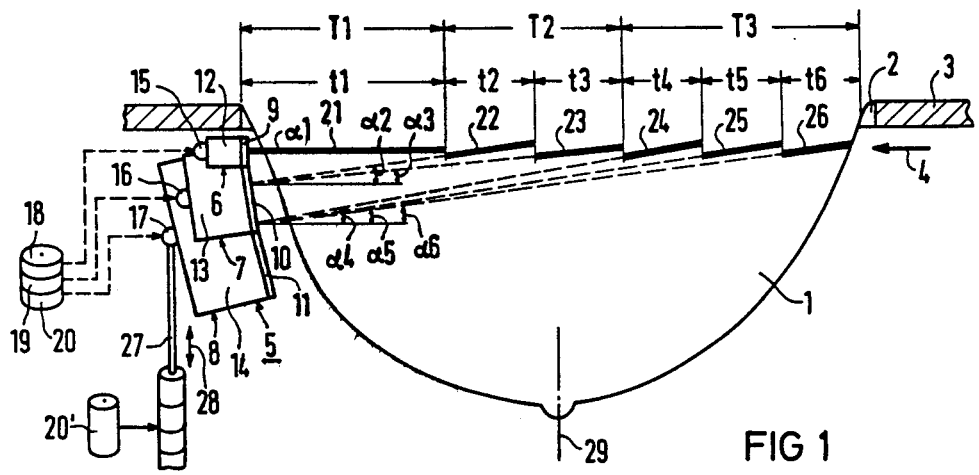
FIG. 1 shows a schematic diagram illustrating the basic concept of this invention.
Figure 3:
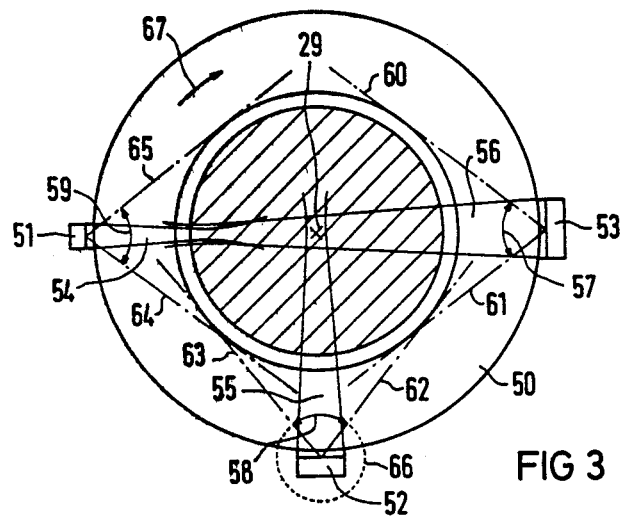
FIG. 3 illustrates a sample embodiment with mechanical sector scanners.

In a FIG. 1 a female breast 1, the object to be examined, extends through the application opening 2 of a board 3 (i.e. part of a patient table, on which a patient has been placed). Arrow 4 indicates a slice plane close to the breast wall, from which an ultrasound transmitting/receiving system 5 is to provide a coronal slice image of tissue situated close to the breast wall. In the present case the ultrasound transmitting/receiving system 5 consists of three ultrasound transducers 6, 7 and 8, which have been installed in one housing. However, these converters can be also arranged in an offset fashion at the perimeter of a ring disk, as illustrated in FIG. 3. In the present case, the ultrasound transducers 6, 7 and 8 are mechanical sector scanners. They include ultrasound transmitting/receiving quartzes 9, 10 and/or 11, which have been arranged on the carrier 12, 13, 14 (as schematically depicted).

Configuration adjustment components for adjusting the direction of the ultrasound waves or lobes emanating from the ultrasound transducers are provided below. The first major characteristics of the ultrasound transducer configuration is found in the swivel capability of the individual ultrasound transducers 6, 7 and 8 provided by means of the horizontal rotating joints 15, 16, 17. By means of a motorized driving system 18, 19 and 20, the individual ultrasound transducers can be adjusted in relation to one another, so that different tilting angles result with respect to the indicated coronal scanning plane close to the breast wall of the object to be examined (in this case the female breast 1). In FIG. 1, the tilting angle of one of the ultrasound transducers is 0° (1=0). Different tilting angles $\alpha 2$ and $\alpha 3$ as well as angles $\alpha 4$ and $\alpha 5$ and $\alpha 6$ have been allocated to the second ultrasound transducer 7 as well as to the third ultrasound transducer 8 respectively. In addition, the entire system 5 can be slowly rotated around axis of rotation 29 (symmetrical axis of breast 1) by means of rotation drive 20'.

The second major characteristic of the ultrasound transducer configuration is found in the different apertures for each of the three ultrasound transducers. The aperture of the smallest ultrasound transducer 6 is such that its transmitting/receiving lobe is focused at surface tissue area T1 of female breast 1. The aperture of the next largest ultrasound transducer 7 is such that the transmitting/receiving lobe is focused at medium depth area T2 of female breast 1. On the other hand, the transmitting/receiving lobe of the ultrasound transducer 8 with the largest aperture is focused at the largest depth area T3 of female breast 1.

Through step by step adjustment of the tilting angle of the respective converter heads and through simultaneous rotation of the system 5 around breast 1 as well as by simultaneous activation of a time gate circuit (according to FIG. 2), the signal data from the area sections 21, 22, 23, 24, 25, and 26 can be acquired section by section in successive time intervals t1, t2, t3, t4, t5 and t6, as seen in FIG. 1. However, the sections 21 through 26 approximate very closely the coronal slice plane close to the breast as indicated by arrow 4. An appropriate computer conversion of the data results in a tomography image of a coronal plane close to the breast wall. Other slice planes parallel to the breast wall are provided by adjusting the height of the system 5 over motor drive system 27 in the direction of arrow 28.

Figure 2:
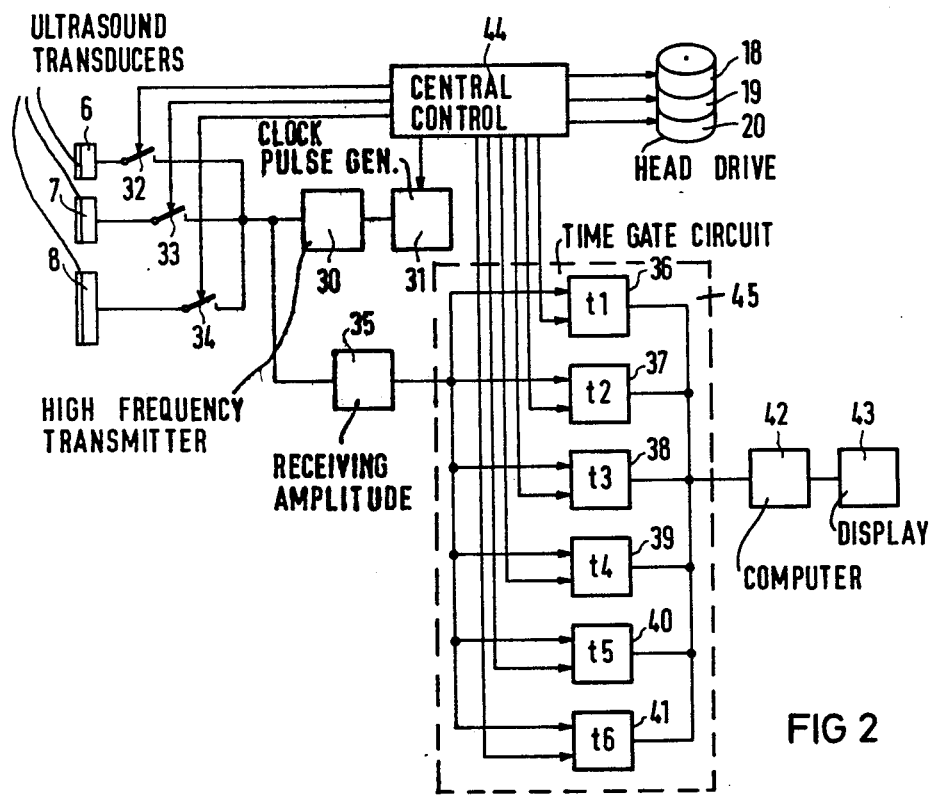
FIG. 2 shows a basic circuit diagram to be applied with this invention.

FIG. 2 provides a basic circuit diagram for controlling the ultrasound transmitting/receiving system 5 depicted in FIG. 1. The individual ultrasound transducers with different apertures are again identified as 6, 7, and 8 in the basic circuit diagram. As is known, the ultrasound transducers are operated with a high frequency transmitter 30 including clock generator 31. Suitable time and position control of the ultrasound transducers is obtained via control switches 32, 33, and 34. The ultrasound echo signals received from the breast 1 during the rotation of the system are forwarded from a receiver amplifier 35 to a time gate circuit 45 including time gates 36 through 41. The time gates 36 through 41 will only allow echo signals to be forwarded section by section to the computer during the times t1 through t6 as illustrated in FIG. 1. From the data selected in this manner, the computer 42 computes the approximated coronal slice image close to the breast wall, which will be displayed on a display device 43. The central system control configuration has been identified with reference No. 44.

The central control circuit 44 preferably is a programmable computer having various output control lines. The computer program may be designed as follows.

In order to start the operation, the height of the transducer 6 is defined and adjusted through the motor 27. The transducer 6 is positioned to take the emission and receiving angle $\alpha 1$. Simultaneously the beam direction of the second transducer 7 is adjusted to take the angle $\alpha 2$, and the beam direction of the transducer 8 is adjusted to take the angle $\alpha 4$. All transducers 6, 7, 8 have the same position (scan position) with respect to an axis going through 15, 16 and 17, respectively, which three axes are parallel to the double arrow 28 shown in FIG. 1.

In a first step, the control circuit 44 will close switch 32. In a subsequent step the control circuit 44 will trigger the clock pulse generator 31 which is turn via high frequency transmitter 30 will cause transducer 6 to emit an ultrasound pulse. As a next step, the control circuit 44 will activate the time gate 36. The echo signal from the depth region 22 equivalent to the time period $t_1$ will be received through transducer 6 and receiving amplifier 35. The echo signal is passed to the time gate 36 and subsequently stored in the computer 42 according to the coordinates within the scanning plane. In a next step the central control circuit 44 will open switch 32 and close switch 33. Now, the central control circuit 44 will trigger the clock pulse generator 32 again. As a result, the transducer 7 will emit an ultrasound pulse in $\alpha 2$ direction. Next control circuit 44 will activate gate 37. Thus, the corresponding echo signal will pass the time gate 37 and will arrive at the computer 42. In other words, the echo signal from a depth region 22 equivalent to the time period $t_2$ is stored in the computer 42 according to the coordinates within the scanning plane.

In a next step the control circuit 44 will open switch 33 and close switch 34. As a consequence, transducer 8 will issue an ultrasound pulse as soon as pulse generator 31 is triggered again. Now the control circuit 44 will activate time gate 39 which corresponds to the time interval $T_4$. The echo signal resulting from the ultrasound pulse will be received by transducer 8 and subsequently passed through gate 39 to the computer 42. This echo signal is derived from a depth region which corresponds to the time period $t_4$. The echo signal is also stored in the memory of the computer 42 according to the scanning coordinates.

Next, the central control unit 44 will cause transducer 7 to assume the emission and receiving angle $\alpha 3$. It will also adjust the position of transducer 8 such that transducer 8 will emit and receive ultrasound in and from angle direction $\alpha 5$, respectively. Now switch 33 is closed, and the central control unit 44 will cause transducer 7 to emit an ultrasound pulse. The corresponding echo signal is received during time period $t_3$ through time gate 38 which has been activated before hand. The echo signal which corresponds to the depth region 23 is passed to the computer 42 and stored therein.

During the next data acquisition cycle, the switch 33 is opened and switch 34 is closed. An ultrasound pulse is emitted through transducer 8, and the resulting echo signal is received during time period $t_5$ via time gate 40. This echo signal is also stored in computer 42.

In the following cycle the transducer 8 takes the angle position $\alpha 6$. The pulse generator 31 is triggered, and the transducer 8 emits an ultrasound pulse into the object 1 under investigation. The control unit 44 opens gate 41 in order that signals from a depth region 26 corresponding to the time interval $t_6$ may pass. This echo signal from the depth region 26 is received by the computer 42 and stored in a suitable location of its memory.

Thus, a plurality of data have been assembled in the computer 42. In a next fundamental step, all three transducers 6, 7, 8 are rotated an increment about the aforementioned axes parallel to the double arrow 28. Each of these axes is perpendicular to the scanning plane. Thus, the three transducers 6, 7 and 8 take a second scanning position. Subsequently the whole procedure as discussed above is repeated step by step. The data received during these various operations are also stored in the computer 42.

It should be noted that typically between 50 and 200 different scanning positions can be assumed. In other words, there may be between 50 and 200 different positions which vary by a predetermined increment with respect to the axes which are parallel to the double arrow 28.

After data have been acquired from all these 50 to 200 scanning positions, the transducers 6, 7 and 8 including the scanning mechanism 15, 16, 17, 27 are rotated by an incremental angle about the axis 29, and the whole scanning procedure as discussed above is repeated. In total, 20 to 200 incremental angle positions with respect to axis 29 may be taken such that the object 1 is examined from all directions. In each of these incremental angle positions, the scanning procedures as discribed before are performed. The data received are also stored in the computer 42. Finally the computer 42 determines a reflection CT image from all these data in a conventional way, and the CT image will be displayed on the screen of the display device 43.

As already mentioned, the three converters shown in FIG. 1, may be also arranged at the perimeter of a ring disk, as depicted in FIG. 3. In FIG. 3 three mechanical sector scanners 51, 52, and 53 are arranged at the edge of a ring disk 50. The tilting angle of these sector scanners can be adjusted to change the directions of the transmitting/receiving lobes 54, 55, and 56 in accordance with FIG. 1. Again these sector scanners are provided with different sized apertures for focusing at different object depths T1, T2 and T3. Furthermore, the ring disk 50 rotates together with the mechanical sectors scanners 51, 52, and 53 around rotation axis 29 extending through breast 1. Sector scan fields can be generated through swivelling of the sector scanners, as displayed in FIG. 1 by the swivel arrows 57, 58, 59 which are bounded by limiting lines 60 to 65 (depicted as dotted lines) of the respective sector field. Similarly, the individual sector scanners may be rotatable scanners, as indicated by the dotted arrow line 66 for sector scanner 52 in FIG. 3. In both cases the ring disk 50 rotation speed of angular frequency is much lower than the angular frequency with which the sector scanner is either swivelled or rotated. For example, the rotation speed of the ring disk which carries the sector scanner is approximately 0.1 Hz. However, the swivel or rotation frequency of the sector scanner ranges between 3 to 4 Hz. The direction of rotation of ring disk 50 is indicated by rotation arrow 67.

Figure 4:
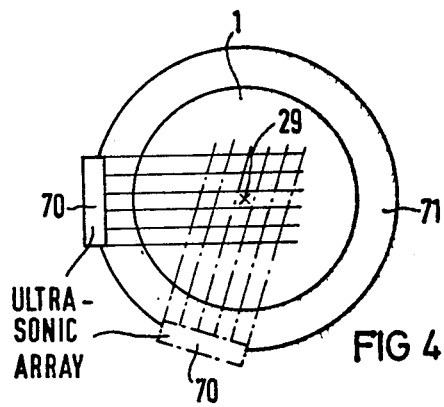
FIGS. 4 and 5 depict a sample embodiment for linear arrays or arrays with electronically generated sector scan.
Figure 5:
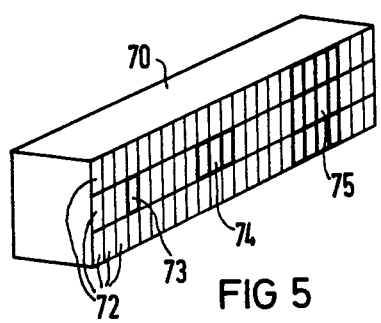

FIG. 4 shows another possible sample embodiment for an ultrasound transmitting/receiving system designed in accordance with the present invention. In FIG. 4 the ultrasound transducer is an ultrasound array 70 (or several of these arrays combined), such as a linear array or an array with electronically controlled beam sweep for sector scanning, which is rotated slowly in a circular path 71 around the axis 29 extending through breast 1. A second rotation position of the ultrasound array 70 has been depicted as a dotted line configuration in FIG. 4. Preferably, the array 70 is a multi-line array, that is to say an array with matrix-like arranged converter elements. FIG. 5 illustrates for example such an array 70 with converter elements 72 tiered at three lines. During the transmitting and/or receiving phase different apertures can be obtained through the usual electronic connection or disconnection of individual transmitting elements to/or from transmitters with different transmitting characteristics. Such an aperture configuration is indicated by the three different sized apertures 73, 74 and 75.

Figure 6:
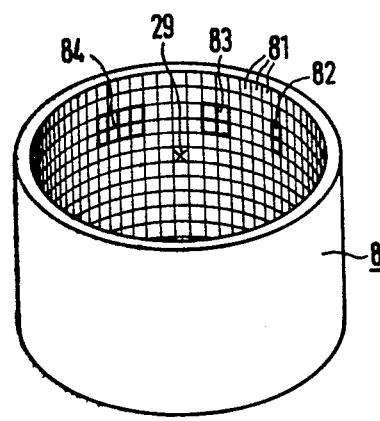
FIG. 6 shows a sample embodiment with ring array.

Finally, FIG. 6 displays an ultrasound transmitting/receiving system designed as a ring array in which the elements 81 are laminarly arranged. The beam sweep and continuous beam switching along the ring array is performed in a purely electronic mode (e.g. in accordance with FIG. 5 of U.S. Pat. No. 4,105,018). Again, the setting of different apertures 82, 83, and 84 is performed as usual by connecting or disconnecting several converter elements within one group.

The ultrasound transducers of FIGS. 1 to 6 radiate directly into the object to be examined. Of course, the present invention also includes embodiments or configurations in which the ultrasound transducer or transducers radiate indirectly into the object to be examined via a mirror or other means.

There has thus been shown and described novel apparatus for ultrasound tomography which fulfills all the objects and advantages sought therefor. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. An ultrasound tomography device having an ultrasound transmitting/receiving system for line scanning of an object to be examined from different angular directions about an axis of rotation, said transmitting/receiving system comprising, in combination:
   (a) ultrasound transducer means for line scanning an object to be examined from different angular directions about said axis of rotation and at different tilting angles with respect to a coronal-plane of said object to be examined;
   (b) adjustable forcusing means, associated with said transducer means, for focusing said transducer means at various object depths in coronal-like scanning planes;
   (c) adjustable positioning means, asociated with said transducer means, for adjusting the tilting angles of the respective transmitting/receiving lobes of said transducer means; and
   (d) time gate circuit means, coupled to said transducer means, for acquiring signal data received by said transducer means from different depths in successive time periods in coordination with the tilting angle of said transducer means, whereby said focusing depths, said tilting angles and said time gated signal acquisition are controlled to provide a coronal like scanning plane of the object to be examined.

2. The ultrasound tomography device as recited in claim 1, wherein at least one of said ultrasound transducers is provided with converter elements, said converter elements being controllable in groups so that said ultrasound transducer is operable in a line scanning mode to permit said object to be examined to be line scanned from different angular directions.

3. The ultrasound tomography device as recited in claim 2, comprised of one such ultrasound transducer and operable as a linear array which is rotatable around said object to be examined.

4. The ultrasound tomography device as recited in claim 2, comprised of one such ultrasound transducer and wherein said ultrasound transducer is an electronically controlled sector scanner array which is rotatable around said object to be examined.

5. The ultrasound tomography device as recited in claim 2, comprised of one such ultrasound transducer, said transducer further comprising an electronically controllable ring array which surrounds said object to be examined and which is controllable to allow continuous switching of said converter elements along the surfaces of said ring array.

6. The ultrasound tomography device as recited in claim 1,
   wherein said positioning means include a ring disk,
   wherein said ultrasound transducers are arranged peripherally around said ring disk in a swivelable mode; and
   wherein said positioning means further comprise tilting means to allow adjustment of the orientation of said transducers with respect to said object to be examined.

7. The ultrasound tomography device as recited in claim 6, wherein said ring disk rotates around said object to be examined.

8. The ultrasound tomography device as recited in claim 1, wherein said focusing means to permit focusing at various object depths comprise apertures of different sizes to realize the various focusing depths.

9. The ultrasound tomography device as recited in claim 8, wherein said differently sized apertures comprise ultrasound transmitting/receiving surfaces of different sizes.

10. The ultrasound tomography device as recited in claim 8,
    wherein said apertures comprise transducers having set outer measurements and a matrix-like arrangement of elements; and
    wherein the number of elements activated determines an aperture size.

11. The ultrasound tomography device as recited in claim 1, wherein said positioning means comprise mechanical means for positioning said ultrasound transducers.

12. The ultrasound tomography device as recited in claim 1, wherein said positioning means comprise electronic means for adjusting and setting the direction of ultrasound waves originating in said ultrasound transducer.

13. The ultrasound tomography device as recited in claim 1, wherein said positioning means comprise both mechanical and electronic means for adjusting and setting the direction of said ultrasound waves.

* * * * *